United States Patent [19]

Hokanson et al.

[11] Patent Number: 5,426,501
[45] Date of Patent: Jun. 20, 1995

[54] APPARATUS AND METHOD FOR PARTICLE ANALYSIS

[75] Inventors: Jon V. Hokanson, Redmond; Barry W. Reed, Auburn, both of Wash.

[73] Assignee: Laser Sensor Technology, Inc., Redmond, Wash.

[21] Appl. No.: 1,382

[22] Filed: Jan. 6, 1993

[51] Int. Cl.$^6$ ............................................. G01N 15/02
[52] U.S. Cl. ................................. 356/335; 250/222.2; 377/11
[58] Field of Search .......................... 356/335; 377/11; 250/222.2, 573

[56] References Cited

U.S. PATENT DOCUMENTS

| | | | |
|---|---|---|---|
| 3,591,290 | 7/1971 | Zinner et al. | 356/335 |
| 3,676,647 | 7/1972 | Staffin et al. | 235/29 PC |
| 3,733,547 | 5/1973 | Coulter et al. | 307/261 |
| 3,781,674 | 12/1973 | Claps | 324/71 CP |
| 3,820,020 | 6/1974 | Doty et al. | 324/71.4 |
| 3,858,851 | 1/1975 | Ogle | 356/102 |
| 3,941,477 | 3/1976 | Schodl | 356/342 |
| 3,998,552 | 12/1976 | Stewart et al. | 356/342 |
| 4,135,821 | 1/1979 | Pechin et al. | 356/335 |
| 4,140,395 | 2/1979 | Kreikebaum | 356/336 |
| 4,348,111 | 9/1982 | Goulas et al. | 356/336 |
| 4,387,993 | 6/1983 | Adrian | 356/336 |
| 4,429,995 | 2/1984 | Goulas | 356/343 |
| 4,434,647 | 3/1984 | Whitcomb et al. | 356/243 |
| 4,492,467 | 1/1985 | Drain et al. | 356/336 |
| 4,497,576 | 2/1985 | Caussignac et al. | 356/336 |
| 4,635,215 | 1/1987 | Friend | 250/222.2 |
| 4,842,406 | 6/1989 | VonBargen | 356/336 |
| 4,871,251 | 10/1989 | Preikschat et al. | 356/336 |
| 5,092,675 | 3/1992 | Sommer | 356/338 |
| 5,122,656 | 6/1992 | Hornung et al. | 250/573 |

FOREIGN PATENT DOCUMENTS

| | | | |
|---|---|---|---|
| 1102580 | 6/1981 | Canada | G01N 21/26 |
| 0289200 | 11/1988 | European Pat. Off. | G01N 15/14 |
| 2642839 | 8/1990 | France | G01N 15/02 |
| 1919628 | 8/1974 | Germany | 421.13/4 |
| 3226906A1 | 1/1984 | Germany | G01N 21/47 |
| 1305923 | 2/1973 | United Kingdom | G01N 15/06 |

*Primary Examiner*—Richard A. Rosenberger
*Attorney, Agent, or Firm*—Christensen, O'Connor, Johnson & Kindness

[57] ABSTRACT

Apparatus and a method are disclosed for determining the sizes of particles entrained in a fluid over a relatively wide range of sizes and determining the distribution of particles in a plurality of size increments. A sample of particles is fed into a drop tube, allowing the particles to be distributed at a relatively low density and fall through a sensing region defined at an intermediate point in the drop tube. A laser diode produces coherent light that is focused with a lens, forming a sheet of coherent light that is directed transversely through transparent sides of the drop tube toward a lens that focuses the sheet of coherent light on a photodetector. A laser intensity control circuit maintains a constant light intensity output from the laser diode when no particle is present in the sensing region and compensates for ambient light. When a particle in the size range of $32\mu$ to $4000\mu$ falls through the sensing region, a chord around the particle is illuminated by the relatively thin sheet of coherent light, and the level of an electrical signal produced by photodetector is reduced in direct proportion to the portion of the sheet of coherent light that is occluded by the particle. A peak value of the pulse is thus a measure of the size of the particle. A pulse discrimination circuit detects pulses produced by a plurality of particles in the sensing region, preventing such multiple particles from being analyzed or counted. After the size of a particle is determined, a counter increments the count in an appropriate channel, each channel corresponding to one of plurality of different successive ranges that together cover the total size range of the particle analyzer.

19 Claims, 4 Drawing Sheets

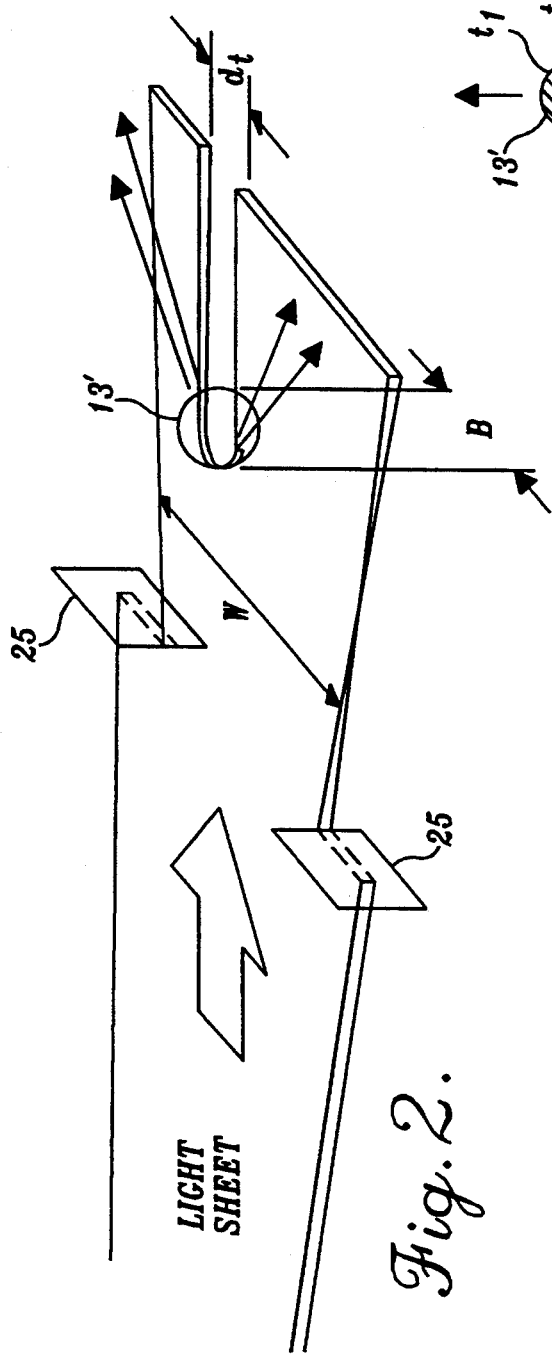
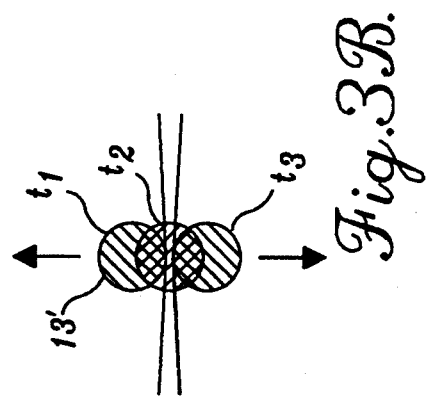
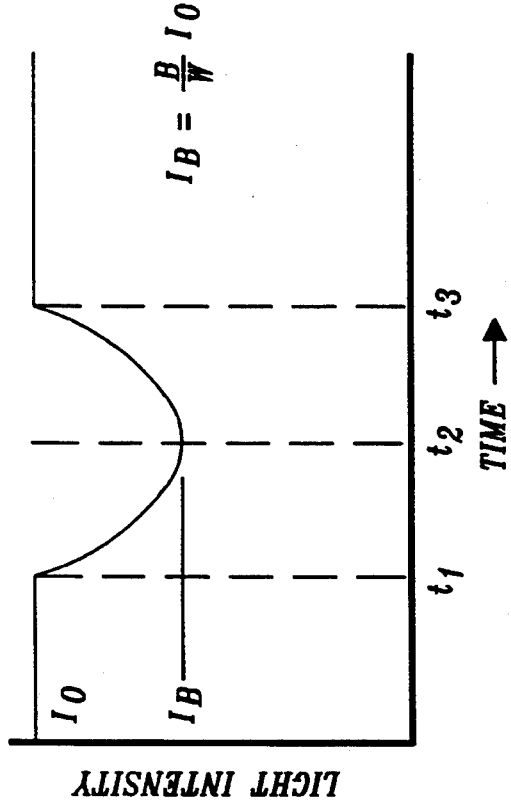
Fig. 2.
Fig. 3B.
Fig. 3A.

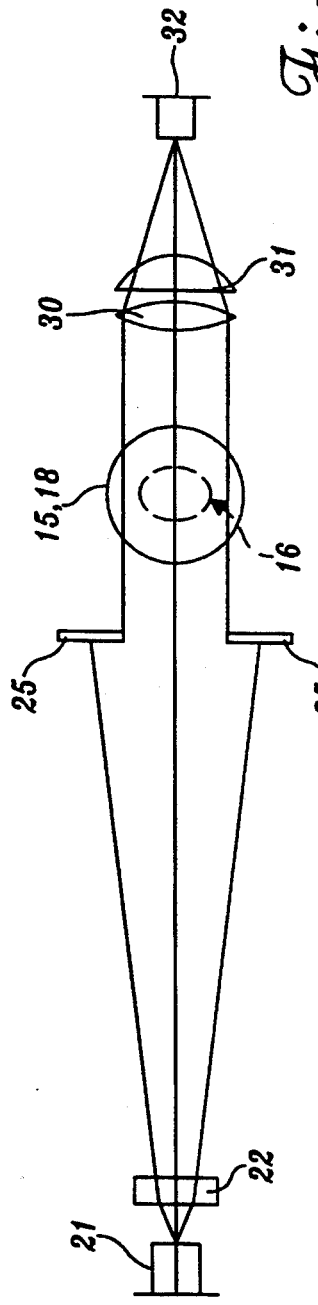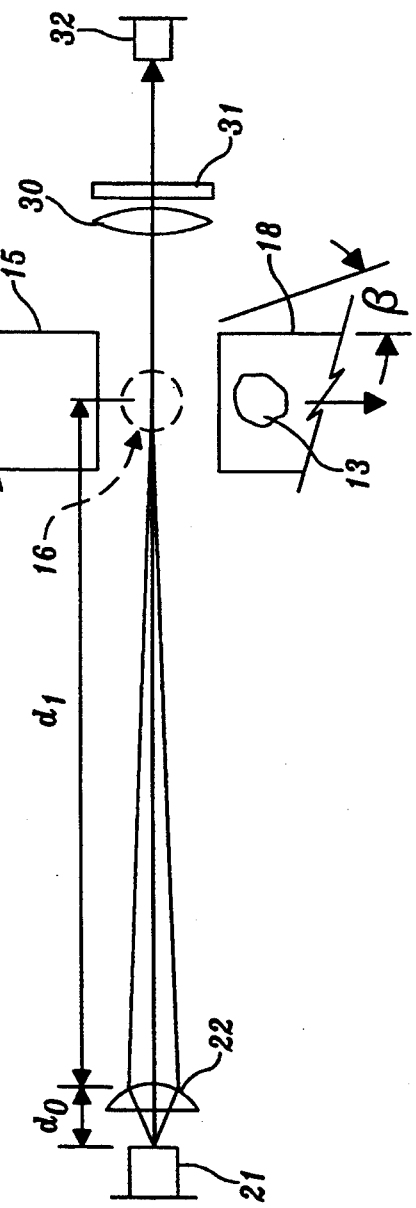

APPARATUS AND METHOD FOR PARTICLE ANALYSIS

FIELD OF THE INVENTION

The present invention relates to apparatus and a method for analyzing the sizes of particles in a fluid medium, and more specifically, to analyzing the size distribution of particles using coherent light.

BACKGROUND OF THE INVENTION

There are many applications in industry and science in which it is required to determine the density of particles suspended in a fluid (i.e., liquid or gaseous) medium, and the sizes or size distribution of such particles. Such measurements can be very important in manufacturing processes in a number of industries, including those related to pharmaceutical, plastics, chemical, food processing, mining, ceramic, and concrete aggregate technologies. Processes such as crystal growth, precipitation, polymerization, gravimetric separation, and grinding must be monitored and/or controlled with regard to the sizes of suspended particles to control the quality of the final product.

While particle size analyzers have traditionally been used as a final quality control tool, recent market studies have shown that customers are increasingly looking at on-line particle size control to make process adjustments so as to prevent off-grade materials from being produced. Specific applications include: (a) the food processing industry, e.g., in monitoring and controlling the dry grinding of flours, coffee, sugar, and other ingredients, any of which can dramatically change the taste properties of food products in which they are incorporated; (b) the coal-fired power industry, where the size of coal dust injected into a power boiler combustion chamber determines the efficiency rating of that boiler and the extent to which noxious by-products like $CO$ and $NO_2$ are produced. In all of these cases, close monitoring of the process materials, in real time, enhances production efficiency, which quickly pays for the capital cost of the particulate size monitoring and control system. To produce such on-line particle size monitoring and control systems, one has to have a reliable and continuously operating measuring system that incorporates a reliable sampling system (to continuously extract material from a production flow line), a sample reduction system to reduce a larger sample to a smaller measurable sample (riffler), and a continuous, automatically operating particle size measuring device.

In the past, a number of different technologies have been used for the analysis of particle size and particle size distribution. The most widely used technique involves screen or sieve analysis. In this technique, a representative sample of a particulate product is poured into a stack of sieves or screens, each screen being attached to the bottom of a tray. The stack of screens is then shaken or vibrated for a predetermined length of time, causing the particles to fall through the screens until the size of the mesh in a particular screen is less than the size of a particle, stopping the particle on that screen. The contents of each tray is then weighed, and the size fraction in each tray is expressed as a percentage of the total weight of the specimen. The screens are arranged in order sequentially by their respective sizes so that the largest particles will be retained on the first screen, the next largest on the second screen, and the smallest particles fall through all of the screens and are collected in a tray at the bottom of the stack of screens. Each of the screens is characterized by specific mesh size. In a standard range, there are 30 different mesh sizes, from mesh size #4, equivalent to a particle diameter of 4.76 mm (0.187 inches) to mesh size #325, equivalent to a particle diameter of 0.044 mm (0.0017 inches). It should be noted that the #325 mesh size is typically the smallest mesh size commonly used; as a consequence, screens are normally used to segregate particles ranging in size from 0.044 mm (0.0017 inches) up to several mm in size. While screens are relatively inexpensive, they have several significant limitations in sizing particulate matter, specifically:

(1) Screens are very labor intensive to use. The procedures for filling the screens, weighing each tray after each screening operation, and cleaning the trays all involve manual operations, which require operator time.
(2) A sieving operation typically only involves up to a maximum of eight size trays, thereby limiting the resolution of the measurement.
(3) The screens wear and have to be replaced periodically.
(4) Screens used in a dry-sieving operation are often affected by electro-static effects. The shaking and vibrations during the sieving operation result in electro-static charge effects that cause the particles to adhere to each other, producing erroneous results.

The second most widely used technique to characterize particle size and size distribution is an optical technique using the Fraunhofer diffraction effect. There are a number of companies making devices based on this technique, e.g., Malvern Ltd. (MASTERSIZER ™), Leeds & Northrup (MICROTRAC II ™), Cilas (GRANULOMETER ™), Coulter Co. (LS 100 ™). These devices use a coherent laser beam to produce a collimated light beam that is transmitted across a sensing region. Particles that flow (or are blown) across this sensing region diffract light from the collimated beam. The diffracted light is scattered out of the collimated light beam and is collected by a set of lenses, which in turn focus this diffracted light onto a plurality of detectors. These detectors are typically arranged in a concentric ring configuration in order to capture all of the light scattered at a given angle. In accordance with standard Fraunhofer diffraction theory, smaller particles scatter light through a larger scattering angle than larger particles. This type of device is best suited to measure particle sizes in the range of $0.5\mu$ (0.0005 mm) to $500\mu$ (0.5 mm, 0.0197 inch).

Laser diffraction devices have several limitations, which make them more costly and difficult to use compared to sieving devices (particularly for particle size measurements above $500\mu$), including the following:

(1) Laser diffraction devices require the light to be transmitted through the sensing zone region from a light source at one side of the sensing zone toward detectors mounted at an opposite side. Therefore, the concentration of particles has to be sufficiently low so that the light is able to penetrate the assemblage of particles suspended in the measuring region. Laser diffraction devices require complex dilution and sample conditioning systems to ensure that the concentration of particles meets this requirement.

(2) The amount of light scattered from larger particles due to Fraunhofer diffraction is, on a percentage basis, much less as compared to smaller particles; also, for larger particles, the scattering angle is very close to 0°, substantially aligned with the direction of propagation of the collimated beam. Consequently, the measuring range for large particles is typically limited to about 500$\mu$ (0.5 mm, 0.0197 inch).

(3) Laser diffraction devices are complex devices, requiring a dedicated computer for data handling, and typically have a cost about 20 times that of simple sieve systems.

Both the sieve and the laser diffraction techniques have significant drawbacks, as described above. The former technique can not readily be automated and the latter technique does not measure the size distribution over the full particulate size range (from 0.031–4.76 mm) covered by standard sieving technique.

A third measuring technique is also based on a light transmission geometry to measure the amount of light that is obscured by individual particles as they pass through an optical sensing region. In such devices (commercially available from several companies, e.g., Climet and Hyac Royco), the size of each particle is proportional to the amount of light obscured by the cross-sectional area of that particle, measured as a percentage fraction of the total cross-sectional area of the sensing region. This relationship is based on area, both the area of a particle (i.e., the product of its cross-sectional length and width) and the area of measuring region. If the size of the particle is 1/100 of the width of the sensing region measured transverse to the light path, then the degree of light obscuration produced by the total surface area of the particle as it passes through the sensing region is $[1/100]^2$, or 1 part in 10,000. This technique typically covers measurement of a particle size ranging from 0.5$\mu$ through 100$\mu$ and is limited to single particle measurements. Because the area of the sensing region is relatively large compared to the area of particles at the low end of the size range, the probability of more than one particle at a time passing through the sensing region is very high. As a practical result, this technique can only be used at very low particle concentrations, e.g., for use as an impurity monitor.

A modification of the light obscuration principle of measurement is disclosed in U.S. Pat. No. 4,842,406 (VonBargen). In this patent, a collimated sheet of light is directed through a sensing region to monitor particles in three size ranges, including 0.5$\mu$ through 10$\mu$, 10$\mu$ through 50$\mu$, and 50$\mu$ through 300$\mu$. The particles in the smallest size range are detected using a first detector that responds to forward scattered light; particles in the mid-size range are detected by a second detector that is disposed transverse to the collimated sheet of light, as a function of the amplitude of pulses produced by the direct beam as a particle intersects the collimated sheet of light. The larger particles in the third range are detected by measuring the duration of pulses in the direct path using the first detector. The patent describes three different measuring techniques that applied to "measure particle sizes most precisely in the entire range from 0.5$\mu$ to 300$\mu$," in other words, to widen the dynamic range of the measurement as much as possible. Still, the described measuring technique is limited in that it (a) only measures single particle events, or relatively low particle concentration (e.g., at the extremes of the size range it can only measure at $[(0.5/300)^2 \times 100=]0.00027\%$ concentration because of the area of the measuring region relative to the area of the particle, as discussed above), (2) requires constant material flow velocity through the measuring region, (3) does not cover the higher size ranges above 300$\mu$, and (4) is not linear over the entire measuring range. The present invention overcomes these limitations by recognizing that as long as the particles passing through the collimated sheet of light have a larger size compared to the thickness of the sheet of light, the size of an individual particle is proportional to the amount of light it obscures as it passes through the sheet of light. Expressed as a percentage fraction of the total line-width of the sheet of light, particle size is simply the size of that portion of the particle that is illuminated by the sheet of light. This relationship is then directly a function of particle size, not, as in the other related light obscuration techniques discussed above, a function of the square of particle size. If the size of the particle is 1/100 of the size of the sensing region, then the amount of light obscuration is indeed 1/100 or 1 part in 100. The advantage of this type of obscuration technology is two-fold: (1) particles pass through a thin sheet of light faster than through a 3-dimensional volume of light, i.e., the coincidence rate is lower, and both higher counting rates and higher material concentrations can be obtained; and (2) a wider dynamic range of particle sizes can be measured.

U.S. Pat. No. 4,842,406 touches on the effect of particles larger than the width of a sheet of light in discussing the detection of particles in the size range from 50 through 300$\mu$, but instead of using an amplitude measurement (indicating the percentage of obscuration caused by a large particle), the patent relies upon a measurement of pulse width or duration. This approach necessarily requires that the material flow speed be maintained very constant. Moreover, the reference does not teach how to avoid errors caused by more than one particle obscuring a portion of the sheet of light at a time. Accordingly, this technique is not usable in applications where higher material concentrations are encountered and where sieves are more commonly used, i.e., in applications where particle sizes range from 44$\mu$ up to several mm.

It is clear that to make full use of the light obscuration technique, it is important to produce a sheet of light, which in the measuring region, is very thin, very wide, and has high uniformity across its entire width, without the diffraction effects normally associated with such light beam configurations. The reasons are as follows: (a) the "thinness" of the light sheet determines the sensitivity to the smallest particle size, (b) the "width" of the sheet determines the maximum particle size that can be measured, and (c) the "uniformity" of the light intensity determines the accuracy of the measurement as a function of the position of a particle across the sheet of light. Diffraction effects are typically caused by using a slit to define the shape of the light beam and produce spurious multiple pulses as a particle falls through the diffracted sheet of light.

The present invention is intended to overcome the limitations and problems in the above-described types of light obscuration systems, including the limitations of the relatively complex, three size range approach disclosed in U.S. Pat. No. 4,842,406, and to provide a cost effective system to fill the void between the particle size and concentration capabilities of existing sieving and laser diffraction techniques. The present invention is further intended to provide a reliable and reproducible technique that can be used by unskilled operators in a standard testing lab environment. It is another objective of this invention to provide a reliable and continuous measuring system for use with a continuously flowing process stream, to provide a continuously updated reading of particle size, so that specific features of the particle size distribution can then be used for process control.

SUMMARY OF THE INVENTION

In accordance with the present invention, apparatus and a method are defined for analyzing particles contained in a fluid, using a light obscuration technique. The apparatus determines the size of discrete particles entrained in a fluid flowing through a sensing region. Each of these particles is classified by size to determine a size distribution. The range of particle sizes extends from about 40$\mu$ to about 4000$\mu$.

The apparatus to determine the size of particles comprises a source of coherent light emitted along a light path. Optical means, disposed in the light path, shape the coherent light into a generally planar sheet of light having a thickness and a width, the thickness being substantially (e.g., three orders of magnitude) less than the width of the sheet of light. Means are provided for conveying a fluid in which the particles are entrained, through the sheet of light. A sensing region is defined within the means where the particles entrained in the fluid intersect and cause at least a partial obscuration of the sheet of light. In response to the fluctuating intensity of the sheet of light passing through the sensing region, which is caused by the particles partially obscuring the light, a light sensor produces an electrical signal indicative of the varying light intensity. The pulse height of this electrical signal is directly and linearly proportional to the illuminated portion (i.e., size of the line width) of a particle as it falls through the sheet of light. Lens means focus the sheet of light on the light sensor; the electrical signal produced by the light sensor includes a pulse having a peak value that indicates a maximum width of a particle as the particle occludes a portion of the sheet of light while passing through the sensing region.

Pulse discriminator means, coupled to the light sensor to receive the electrical signal, discriminate between a pulse produced by a single particle and a pulse produced by a plurality of particles. In response to this difference, the pulse discrimination means suppress a particle count when a plurality of particles pass through the sensing region at the same time. Counter means, coupled to the light sensor and to the pulse discriminator means, count particles to determine a particle size distribution. If the pulse discriminator means determine that said corresponding pulse was produced by only a single particle passing through the sensing region at a time, the counter means register an additional count in one of a plurality of different predefined size ranges as a function of the peak value of a corresponding pulse produced by the light sensor.

Preferably, the apparatus for determining sizes of particles further comprises light control means, coupled to the source of coherent light and to the light sensor to receive the electrical signal, for controlling an intensity of the coherent light emitted by the source of coherent light so that the electrical signal produced by the light sensor is maintained at a predefined level when there are no particles within the sensing region. Also, the counter means preferably comprise a display that graphically represents the particle size distribution. The display graphically represents a plurality of channels, each channel corresponding to one of the plurality of different size ranges. The counter means accumulate counts of particles passing through the sensing region, each particle thus counted in one of the size ranges having a size within that size range; the display graphically represents the number of particles in each size range.

The counter means preferably comprise a circuit board that is adapted to interface with a bus in a personal computer, and the display comprises a video monitor for the computer. Further, the pulse discrimination means preferably comprise a peak detection circuit, and means for determining whether the peak of a pulse is centered between a beginning point and an end point of the pulse, within predefined limits.

The optical means comprise a cylindrical lens that focuses the light from the coherent source to form the sheet of coherent light. Also included in the apparatus are feed means, coupled with the means for conveying the fluid, for feeding the particles into the fluid to flow through the sensing region. In the preferred form of the invention, the fluid comprises an airstream. A fan then draws air, with particles entrained therein, through the sensing region. The means for conveying the fluid comprise a vertical tube having optically transparent slits adjacent to the sensing region, so that the sheet of coherent light passes through the sides of the tube. A negative air pressure within the vertical tube (relative to an external ambient air pressure) prevents the particles flowing through the tube from collecting on the optical means.

The method for determining the size of particles entrained in a fluid includes steps generally consistent with the functions of the elements comprising the apparatus described above.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 illustrates the relationship between the sheet of light and a particle passing through a focal point of the sheet of light;

FIGS. 3A and 3B show the relationship between light intensity and a particle dropping through the sheet of coherent light as a function of time, which produces a negative pulse having a peak value proportional to the size of the particle;

FIG. 4 shows the different optical components along the light path using a top view;

FIG. 5A shows the different optical components along the light path using a side view;

FIG. 5B shows the sensing region of FIG. 5A enlarged; and

DETAILED DESCRIPTION OF THE PREFERRED EMBODIMENT

Overview of the Particle Analyzer

Figure 1:
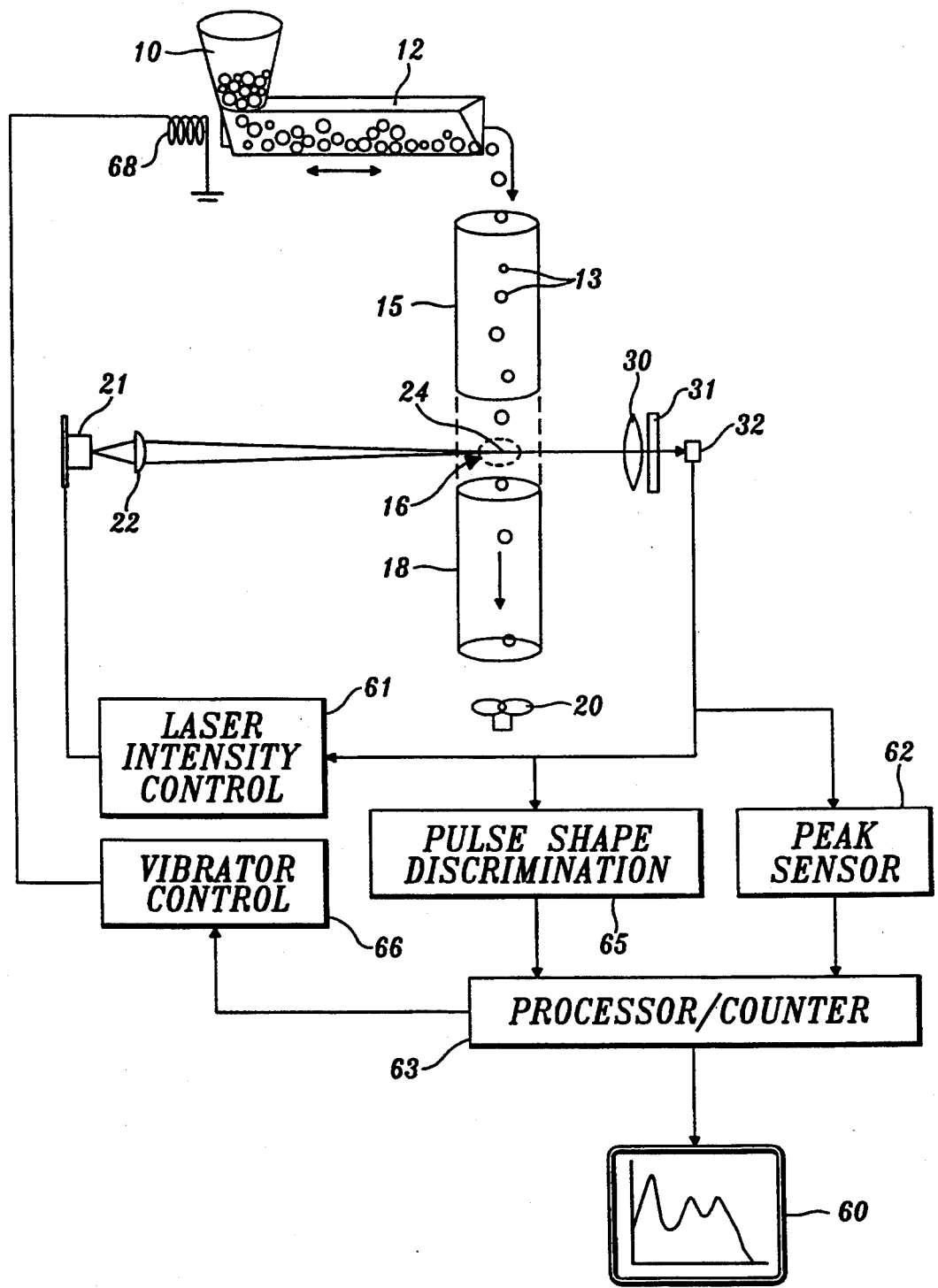
FIG. 1 is a schematic diagram of the particle analysis system of the present invention.

The particle size analysis apparatus of the present invention is illustrated in schematic form in FIGS. 1 and 2. FIG. 1 shows a sample of particles contained in a hopper 10 being discharged through a vibratory feed trough 12. The particles 13 drop into a vertically positioned drop tube 15, and fall through a sensing region 16, flowing with the air in which the particles are entrained, into a lower portion 18 of the drop tube. To simplify the drawing, the lower portion of the drop tube is shown separate from the part into which the particles are fed; however, it will be understood that drop tube 15 is optically transparent, at least adjacent sensing region 16. In the preferred embodiment, the drop tube includes optically transparent slits (not separately shown) adjacent sensing region 16.

The flow of particles through the sensing region is aided by the force of gravity. If desired, an optional variable speed fan 20, disposed in lower portion 18 of the drop tube can be used to pull smaller particles entrained in air through the sensing region, creating a negative air pressure in the tube relative to an external ambient pressure, which prevents particles entrained in the air stream within the tube from collecting on the optical components of the system. As the particles are accelerated by the force of gravity (and/or by fan 20), the particles tend to disperse in the airstream so that particles preferentially pass through the sensing region as individual particles. The present invention is readily modified to count particles entrained in a liquid, as will be apparent to those of ordinary skill in the art.

A laser diode 21 (in the preferred embodiment, a Toshiba ™ type TOLD 9215) provides about 10 milliwatts of continuous light output. The coherent light is emitted from a small area measuring only 0.9 by 2.5 microns in size, at a wavelength of 0.66$\mu$. The coherent light from laser diode 21 is focused into a very thin sheet of light by a cylindrical focusing lens 22, arranged so that the light will spread out in the horizontal plane, but will be focused in the vertical plane, with a focal line point 24 at the center of the sensing region.

FIG. 2 shows that the light pattern at this sensing region forms the above-noted sheet of light having a width spread across the horizontal plane. Two spaced-apart vertical constraints 25 further define a width W for this sheet of light. The width W defines the maximum size particle and the thickness of the sheet of coherent light in the sensing region represents a minimum size of particle that can be analyzed (for size and size distribution) by the particle analyzer. In the preferred embodiment, the maximum size particle is about 4000$\mu$. After this sheet of coherent light passes through sensing region 16, it is focused by a spherical lens 30 and a cylindrical lens 31, so that all of the light from the sheet of light falls on a photodetector 32.

The signal output from photodetector 32 is conveyed to a laser intensity control circuit 61, which maintains the peak intensity of the coherent light produced by laser diode 21 constant to within $\pm 1$ part per million. This control circuit, which is only operational when a particle is not in sensing region 16, samples the output signal from photodetector 32 and compares the signal with a predefined voltage source (not separately shown) to keep the light intensity constant. This same circuit has the additional function of performing an ambient light correction at the beginning of each measurement. This second function is achieved by momentarily turning off the laser diode to determine the output signal level of photodetector 32 under only ambient light conditions; the output signal of the photodetector at that time determines a background light correction used by laser intensity control circuit 61 in controlling the coherent light intensity produced by the laser diode. Laser intensity control circuit 61 thus responds to variations in the laser diode output and any changes in the sensitivity of photodetector 32 over time, and also corrects for any other variables in the system that would affect the output signal produced by photodetector 32 when particles are not present in the sensing region, e.g., dirt build-up on the lenses.

Photodetector Pulse Produced by a Particle

Photodetector 32 responds to a change in the intensity of the sheet of coherent light (after focusing), due to obscuration caused by a particle passing through the sensing region, producing a corresponding electrical signal. In FIGS. 3A and 3B, a pulse is shown as a function of time, for a spherical particle 13' of diameter B moving through the sheet of light in the sensing region. As can be seen in FIG. 3A, at time $t_1$, the particle enters the sheet of light. At time $t_2$, the particle is halfway through the sensing region, so that the sheet of light defines a line on the particle that extends along a diametrical chord about the center of the spherical particle; and, at time $t_3$, the particle leaves the sheet of light. The point of minimum light intensity (maximum light obscuration) at photodetector 32 occurs at time $t_2$, when the particle is halfway through the sheet of light. At that point, the intensity has fallen off from its non-occluded value $I_O$ to a (negative) peak value $I_B$, defined by the following equation:

$$I_B = B/W * I_O \qquad (1)$$

The output signal from photodetector 32 is also coupled to a peak sensing circuit 62, and to a processor/counter circuit 63. The processor/counter comprises a 256 channel counter implemented in software on a circuit board having terminals (not separately shown) adapted to mate with the bus of a personal computer (PC)—also not separately shown. A display 60 is coupled to the processor/counter to provide a graphical display of the size distribution of particles in a sample processed by the particle analyzer. After the size of a particle passing through sensing region 16 is determined as will be explained below, a count in one of the 255 counter channels corresponding to a size range in which the size of the particle lies is incremented by one. (Note that the lowest channel of 256 available channels in the counter is disregarded to eliminate spurious noise counts.) In the preferred embodiment, each of the 255 size channels encompasses a 16$\mu$ incremental size, the 255 size channels together covering particle sizes ranging from 32$\mu$ to 4096$\mu$. After a sample is analyzed, display 60 (which, in the preferred embodiment, comprises the video monitor of a personal computer in which the processor counter is installed) graphically shows the count of particles in each channel or incremental size range, i.e., the monitor displays the size distribution of particles.

The output signal from peak sensing circuit 62 is input to a pulse shape discrimination circuit 65, which evaluates the symmetry of a pulse to determine if the pulse was caused by a single particle or by a plurality of particles occluding a portion of the sheet of light at one time. (Both peak sensing circuit 62 and pulse shape discrimination 65 are also on the PC board.) If a pulse is caused by a plurality of particles passing through the sensing region at one time, the peak of the pulse is substantially offset from a point midway between the beginning and end of the pulse, causing the pulse to be non-symmetrical about the peak value by more than a predefined amount. Pulse shape discrimination circuit 65 inhibits processor/counter circuit 63 from counting any pulse caused by a plurality of particles, since the size of such plural particles can not be accurately determined from the pulse.

In addition to counting particles by size distribution, the processor/counter circuit determines a ratio of good to bad pulses (i.e., the ratio of pulses caused by a single particle relative to pulses caused by a plurality of particles in the sensing region) and provides a control signal that is input to a vibrator control unit 66, which controls a vibration level of an electro-magnetic vibrator coil 68 that develops a vibrational force to feed particles from the sample through vibratory feed trough 12 into the drop tube. As the vibration amplitude of the electro-magnetic vibrator coil is decreased, fewer particles from the sample are fed into the drop tube 15 per unit time, and the density of particles passing through the sheet of coherent light in sensing region 16 is reduced.

FIG. 4 shows a top view and FIG. 5 shows an elevational side view of the path followed by the coherent light emitted from the laser diode. The coherent light passes through cylindrical lens 22, between vertical constraints 25, into sensing region 16, and is focused by lenses 30 and 31 onto photodetector 32. Lens 31 focuses the coherent light in the vertical plane so that all of the light will come to a focus at photodetector 32.

It is important to note that a point light source is used to produce the coherent light in the particle analyzer. Laser diode 21 in the preferred embodiment emits coherent light from an elliptically shaped area, having major and minor axes. When the minor axis is aligned vertically, the coherent light is emitted with a beam divergence of about 28°. The waist of that beam, at its narrowest point, is determined by the object size, in this case, the minor axis (0.9μ) of the elliptically shaped emitting area times the ratio of image distance $d_i$ to object distance $d_o$. In the preferred embodiment, lens 22 is placed close to the laser diode and positioned as far as practical apart from sensing region 16. With a typical ratio of image distance to object distance of about 25, the size of the beam waist 17 is about 22μ. It is important to note that this relatively thin sheet of light is obtained without the use of any narrow beam defining slits. This configuration eliminates diffraction effects that occur with other types of optical configurations, which use a collimated beam and light defining slit to produce a relatively thin sheet of light. Using a point light source, as herein described, produces a very clean light beam of high light intensity and good uniformity within the sensing region. Using a laser diode with relatively high light intensity has the additional advantage that photodetector 32 requires only modest gain, and ambient light intensities are typically only a small fraction of the total coherent light intensity produced by the laser diode as monitored at the photodetector. Consequently, the particle analyzer can be used in full daylight without light shielding.

While the use of a laser diode is herein described, other types of point light sources could also be employed in the alternative. For example, a helium neon laser source, which is spatially filtered by focusing the light beam through a pin hole, could be used. In that case, the pin hole becomes the new "object."

It should also be noted that the principle with which particle size is measured as described above can also be employed in apparatus having a much wider sheet of coherent light. Increasing the width of the sheet of coherent light enables measurement of much larger sized particles over several centimeters in diameter, e.g., crushed rock materials, as typically encountered in the mining and aggregate industries.

Figure 6A:
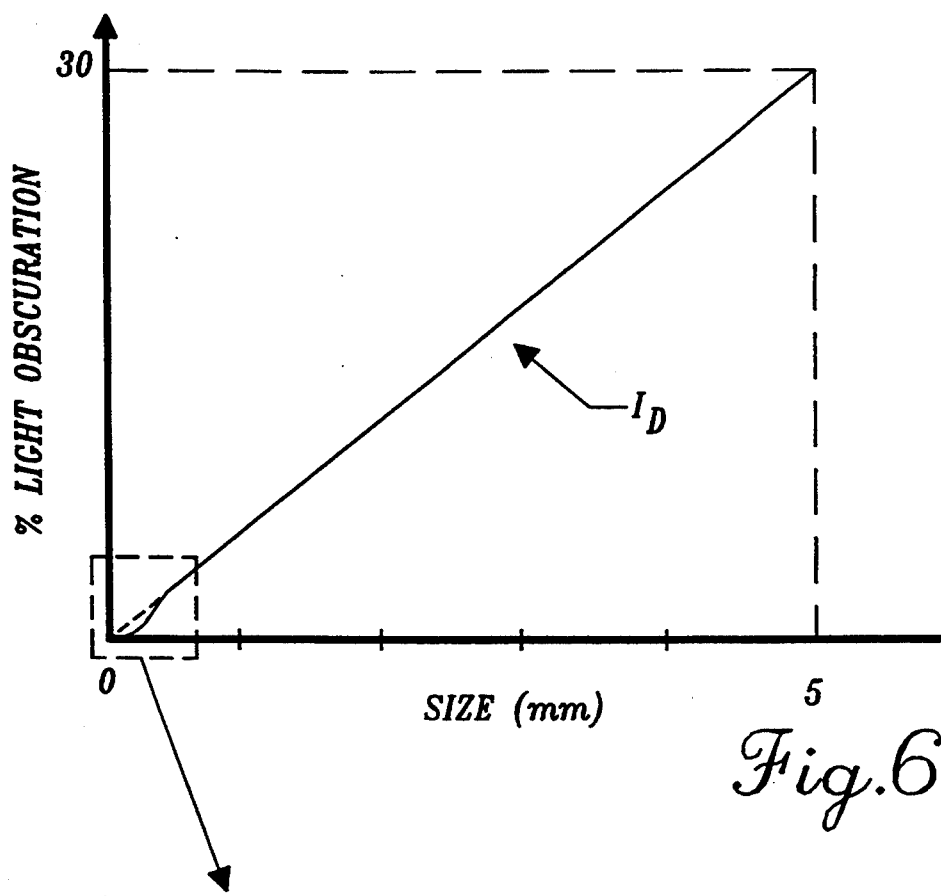
FIGS. 6A and 6B show the percent of light obscuration as a function of particle size for both the direct light beam and the scattered light beam.
Figure 6B:
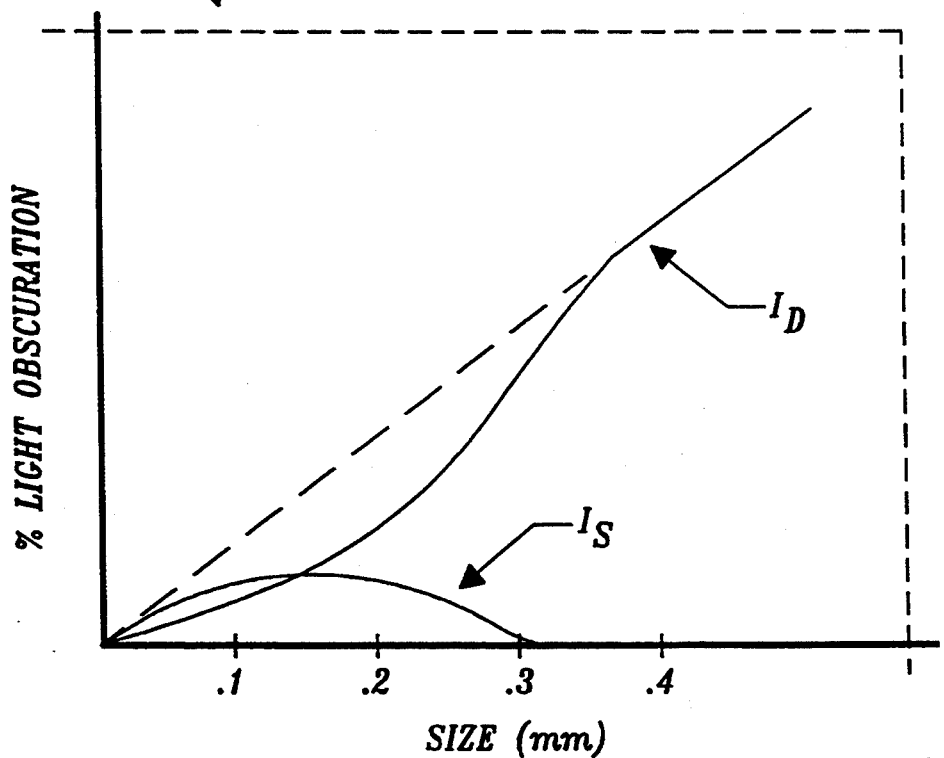

FIG. 6A shows that at particle sizes above about 300 micron (0.0117 inch), the amount of coherent light obscuration by a particle is directly and linearly proportional to particle size, measured around a chord of the particle illuminated by the sheet of coherent light. FIG. 6B shows that for particle sizes less than 300μ, diffraction effects come into play, causing some of the light to be diffracted (bent) around a particle as it passes through the sheet of coherent light, giving the particle the appearance of being smaller than it actually is. This relationship is shown as graph $I_D$, where the curve dips below the theoretically ideal curve, which is shown as a discontinuous or dash line. Processor/counter 63 compensates for the non-linear relationship due to diffraction, when determining the size of particles smaller than 300μ.

The stability of the measurement and the range of particle sizes that can be measured with the present technique depend on the overall stability of the light source and light monitoring path. In some applications, it may be necessary, for example, to determine particle sizes/distribution in a range from 10μ to 5.0 mm. To obtain an accuracy of 0.1%, it is necessary to maintain the light beam intensity constant to within one part in 500,000! This level of stability is achievable by using a feedback signal to stabilize the output intensity of laser diode 21. As noted above, to control the intensity of coherent light produced by laser diode 21, a direct current (DC) signal output from photodetector 32 when there is no particle present in sensing region 16 is compared to a reference voltage, producing a differential signal, which is then used to control the light intensity output from the laser diode. Laser intensity control circuit 61 also compensates for dirt build-up on the optical surfaces of lenses 22, 30, and 31, which causes a decrease in the light transmission, and for changes in the output of the laser diode due to ambient temperature.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. Apparatus for determining sizes of particles entrained in a fluid, where the sizes of the particles generally can be in a range from about 40μ to about 4000μ, comprising:

(a) a source of coherent light emitted along a light path;

(b) optical means, disposed in the light path, for shaping the coherent light into a generally planar sheet of light having a thickness and a width, said thickness being substantially less than said width of the sheet of light;

(c) means for conveying a fluid in which particles are entrained, through the sheet of light, a sensing region being defined within said means where the particles entrained in the fluid intersect said sheet of light;

(d) a light sensor that produces an electrical signal proportional to an intensity light incident on the light sensor;

(e) lens means, for focusing the sheet of light on the light sensor, the electrical signal produced by said light sensor including a pulse having a peak value that indicates a maximum width of a particle as said particle occludes a portion of the sheet of light while passing through the sensing region;

(f) pulse discriminator means, coupled to the light sensor to receive the electrical signal, for discriminating between a pulse produced by a single particle and a pulse produced by a plurality of particles, and in response thereto, producing a particle count suppression signal when a plurality of particles pass through the sensing region at the same time, said pulse discriminator means comprising a peak detection circuit and means for determining whether the peak of a pulse is centered between a beginning and an end point of the pulse, within predefined limits; and (g) counter means, coupled to the light sensor and to the pulse discriminator means, for counting particles to determine a particle size distribution, said counter means registering an additional count in one of a plurality of different predefined size ranges as a function of the peak value of a corresponding pulse produced by the light sensor, if the pulse discriminator means determine that said corresponding pulse was produced by only a single particle passing through the sensing region at a time.

2. The apparatus of claim 1, further comprising light control means, coupled to the source of coherent light and to the light sensor to receive the electrical signal, for controlling an intensity of the coherent light emitted by the source of coherent light so that the electrical signal produced by the light sensor is maintained at a predefined level when a particle is not within the sensing region.

3. The apparatus of claim 1, wherein the counter means comprise a display that graphically represents the particle size distribution.

4. The apparatus of claim 3, wherein the display graphically represents a plurality of channels, each channel corresponding to one of the plurality of different size ranges, said counter means accumulating counts of particles passing through the sensing region, each particle thus counted in one of the size ranges having a size within said one size range, said display graphically representing the number of particles in each size range.

5. The apparatus of claim 3, wherein the counter means comprise a circuit board that is adapted to interface with a bus in a personal computer, and said display comprises a video monitor for the computer.

6. The apparatus of claim 1, wherein the optical means comprise a cylindrical lens.

7. The apparatus of claim 1, further comprising feed means, coupled with the means for conveying the fluid, for feeding the particles into the fluid to flow through the sensing region.

8. The apparatus of claim 1, wherein the fluid comprises an airstream, further comprising a fan that draws air with particles entrained in the air, through the sensing region.

9. The apparatus of claim 1, wherein the means for conveying the fluid comprise a vertical tube having optically transparent slits adjacent the sensing region, so that the sheet of coherent light passes through the sides of the tube.

10. The apparatus of claim 9, wherein the vertical tube has a negative air pressure relative to an ambient air pressure, so that the particles flowing through the tube are prevented from collecting on the optical means.

11. A method for determining the size of particles conveyed by a fluid through a sensing region, comprising the steps of:

(a) transmitting a sheet of coherent light through the sensing region so that the particles conveyed by the fluid are partly illuminated by the sheet of coherent light, which sweeps across the particles as the particles pass through the sensing region;

(b) focusing the sheet of coherent light on a light sensor, after the sheet of coherent light has passed through the sensing region;

(c) detecting an intensity of the sheet of coherent light with the light sensor, producing an electrical pulse having a peak corresponding to a size of a particle across a widest portion of the particle illuminated by the sheet of light as the particle passes through the sensing region, said particle thus occluding a variable portion of the sheet of light as a function of a width of the portion of the particle being scanned by the sheet of coherent light;

(d) monitoring a shape of the pulse to discriminate between a pulse produced by a plurality of particles passing through the sensing region at the same time and only one particle passing through the sensing region at a time, said step of monitoring including the step of detecting a peak of a pulse and determining whether the peak of the pulse is centered between a beginning and an end point of the pulse, within predefined limits; and (e) counting only pulses produced by a single particle passing through the sensing region at a time in a plurality of counters, each of the plurality of counters corresponding to a different size range of particles, and each counter being incremented only when a particle of a size lying within the size range of that counter passes through the sensing region.

12. The method of claim 11, wherein the step of detecting comprises determining a change in the intensity of the sheet of coherent light when partially occluded by a particle, compared to its intensity when not occluded by a particle.

13. The method of claim 11, wherein the step of transmitting comprises the step of focusing a beam of coherent light to define the sheet of coherent light, said sheet having a thickness that defines a minimum size of particle that is thus determined.

14. The method of claim 11, further comprising the step of controlling the intensity of the sheet of coherent light when not occluded by a particle to maintain a predefined intensity.

15. The method of claim 11, wherein the step of counting comprises the step of determining a size distribution of particles passing through the sensing region.

16. The method of claim 15, wherein the step of determining comprises the step of counting particles in each of a plurality of different size ranges.

17. The method of claim 11, further comprising the step of feeding particles from a sample into the fluid over a period of time, so as to disperse the particles flowing through the sensing region.

18. The method of claim 11, further comprising the step of vibrating a sample of the particles to entrain particles in the fluid.

19. The method of claim 11, wherein the fluid comprises air, further comprising the step of providing a fan to draw particles entrained in the air through the sensing region.

* * * * *